United States Patent [19]

Otterbach et al.

[11] Patent Number: 5,386,053
[45] Date of Patent: Jan. 31, 1995

[54] MULTISTEP, CONTINUOUS PREPARATION OF ORGANIC POLYISOCYANATES

[75] Inventors: Andreas Otterbach, Frankenthal, Germany; Hans V. Schwarz, Baton Rouge, La.; Franz Merger, Frankenthal, Germany; Wolfgang Schwarz, Otterstadt, Germany; Eckhardt Brandt, Schifferstadt, Germany; Peter Magnussen, Bad Durkheim, Germany; Otto Mattner, Speyer, Germany

[73] Assignee: BASF Aktiengesellschaft, Ludwigshafen, Germany

[21] Appl. No.: 28,009

[22] Filed: Mar. 8, 1993

[30] Foreign Application Priority Data

Apr. 21, 1992 [DE] Germany .................... 4213099

[51] Int. Cl.⁶ .......................... C07C 263/06
[52] U.S. Cl. ...................... 560/344; 560/345
[58] Field of Search .................... 560/344, 345

[56] References Cited

U.S. PATENT DOCUMENTS

| | | | |
|---|---|---|---|
| 4,530,796 | 7/1985 | Mattner et al. | 560/344 |
| 4,596,678 | 1/1986 | Merger et al. | 560/344 |
| 4,596,679 | 6/1986 | Hellbach | 560/344 |
| 4,692,550 | 9/1987 | Engbert et al. | 560/345 |
| 5,087,739 | 2/1992 | Bohmholdt et al. | 560/345 |
| 5,210,284 | 5/1993 | Mizla et al. | 560/345 |

Primary Examiner—José G. Dees
Assistant Examiner—Samuel Barts
Attorney, Agent, or Firm—Paul L. Marshall

[57] ABSTRACT

A multistep process for the continuous preparation of organic polyisocyanates, preferably aliphatic or cycloaliphatic diisocyanates, by reacting the corresponding organic polyamines with carbonic acid derivatives and alcohols to give monomeric polyurethanes and pyrolyzing the latter involves separating the resultant polyisocyanates and worthless residues in certain reaction steps and recycling the reusable by-products into earlier steps.

10 Claims, No Drawings

MULTISTEP, CONTINUOUS PREPARATION OF ORGANIC POLYISOCYANATES

The present invention relates to a multistep process for the continuous preparation of organic, distillable polyisocyanates, preferably aliphatic or cycloaliphatic diisocyanates, by reacting the corresponding organic polyamines with carbonic acid derivatives and alcohols to give low-molecular-weight, monomeric polyurethanes, and pyrolyzing the latter, in which the resultant polyisocyanates and worthless residues are separated in certain reaction steps, and reusable by-products and intermediates are recycled into earlier steps.

The industrial processes for the preparation of organic polyisocyanates, e.g. aromatic, aliphatic or cycloaliphatic polyisocyanates, are based on phosgenation of the corresponding organic polyamines to give polycarbamic acid chlorides, and thermolysis thereof to give the polyisocyanates and hydrogen chloride. Apart from serious environmental, disposal and safety problems accompanying the use of phosgene, these processes have further crucial disadvantages. Thus, the relatively high basicity of the starting polyamines means that the preparation of aliphatic or cycloaliphatic polyisocyanates only occurs in quite moderate space-time yields. A further disadvantage is the formation of undesired by-products, which can, even in traces, result in considerable discoloration of the polyisocyanates. In the preparation of hexamethylene 1,6-diisocyanate (HDI), for example, a number of by-products are formed, of which the most important, 6-chlorohexyl isocyanate, additionally has the disadvantage of requiring considerable distillative effort for separation from HDI.

Particular problems in this procedure are the high conversion of chlorine into hydrogen chloride via phosgene and carbamoyl chloride, the toxicity of the phosgene, and the corrosive properties of the reaction mixture, the lability of the solvents which are generally employed, and the formation of halogen-containing residues.

There has therefore been no lack of attempts to prepare organic isocyanates, preferably aromatic and (cyclo)aliphatic diisocyanates and/or higher-functional polyisocyanates, by a phosgene-free process.

According to EP-A-0 018 588 (U.S. Pat. No. 4,497,963), aliphatic and/or cycloaliphatic diurethanes and/or polyurethanes are prepared by reacting primary aliphatic and/or cycloaliphatic diamines and/or polyamines with O-alkyl carbamates in the presence of alcohols in an amine $NH_2$ group:carbamate:alcohol ratio of from 1:0.8 to 10:0.25 to 50 at from 160° to 300° C. in the presence or absence of catalysts, and, if necessary, removing the resultant ammonia. The resultant diurethanes and/or polyurethanes can, if desired, be converted into the corresponding diisocyanates and/or higher-functional polyisocyanates. Detailed reaction conditions for the thermolysis are not disclosed in the patent specification.

According to EP-A-28 338 (U.S. Pat. No. 4,290,970), aromatic diisocyanates and/or polyisocyanates are prepared by a two-step process in which, in the first step, primary aromatic diamines and/or polyamines are reacted with O-alkyl carbamates in the presence or absence of catalysts and in the presence or absence of urea and alcohol to give aryldi- and/or -polyurethanes, the resultant ammonia is removed if desired, and the resultant aryldi- and/or -polyurethanes are converted, in the second reaction step, into aromatic diisocyanates and/or polyisocyanates by thermolysis.

Other publications relate to the partial substitution of urea and/or diamines by carbonyl-containing compounds, for example N-substituted carbamates and/or dialkyl carbonates, or mono- or disubstituted ureas or polyureas (EP-B-27 952 (U.S. Pat. No. 4,388,238), EP-B-27 953 (U.S. Pat. No. 4,430,505), EP-B-28 331 (U.S. Pat. No. 4,480,110), EP-A-126 299 (U.S. Pat. No. 4,596,678), EP-A-126 300 (U.S. Pat. No. 4,596,679)).

EP-A-0 320 235 describes a process for the preparation of aliphatic O-arylurethanes by reacting (cyclo)aliphatic polyamines with urea and aromatic hydroxyl compounds.

Although the thermolysis of (cyclo)aliphatic and in particular aromatic monourethanes and diurethanes to give the corresponding isocyanates and alcohol has been known for some time and can be carried out either in the gas phase at elevated temperature or in the liquid phase at comparatively low temperature, it is, in particular, the undesired side reactions and in particular the tendency of the reaction mixtures to form deposits, resins and blockages in the reactors and work-up equipment that impair the economic efficiency of the processes in the long term.

Numerous patent applications therefore describe, for example, chemical methods, e.g. the use of specific catalysts (DE-C-1 022 222 (U.S. Pat. No. 2,692,275) or DE-B-19 44 719 (U.S. Pat. No. 3,734,941)) or catalysts in combination with inert solvents (U.S. Pat. No. 3,919,279 or DE-A-2 635 490 (U.S. Pat. No. 4,081,472)), for improving the yield in the thermolysis of urethane.

The thermolysis of hexamethylene-1,6-diethylurethane under pressure in the presence of dibenzyltoluene as solvent and in the presence of a catalyst mixture comprising methyl toluenesulfonate and diphenyltin dichloride for the preparation of hexamethylene 1,6-diisocyanate is described, for example, in DE-A-3 108 990 (U.S. Pat. No. 4,388,246). No details are given on the preparation and isolation of the starting component and the purification and any recovery of the solvent and of the catalyst mixture, and it is therefore not possible to judge the economic efficiency of the process.

According to EP-B-0 078 005 (U.S. Pat. No. 4,482,499), urethanes can easily be cleaved into the isocyanate and alcohol in a carbon-containing fluidized bed without using a catalyst. According to DE-A-32 27 748 (U.S. Pat. No. 4,613,466), hexamethylenedialkylurethanes can be cleaved to give hexamethylene diisocyanate in the gas phase at above 300° C. in the presence or absence of gas-permeable packing materials, for example made of carbon, steel, brass, copper, zinc, aluminum, titanium, chromium, cobalt or quartz. According to DE-A-32 48 018 (U.S. Pat. No. 4,613,466), this process is carried out in the presence of hydrogen halides and/or hydrogen halide donors.

However, this process cannot achieve a yield of hexamethylene diisocyanate of >90%, since the cleavage products partially recombine. The necessary purification of the hexamethylene 1,6-diisocyanate by distillation may further increase the yield losses.

Furthermore, EP-A-54 817 (U.S. Pat. No. 4,386,033) discloses that monocarbamates can be cleaved in good yields at relatively low temperatures, preferably under reduced pressure, in the presence or absence of catalysts and/or stabilizers and without using solvents. The cleavage products (monoisocyanate and alcohol) are removed from the boiling reaction mixture by distillation and are collected separately by fractional condensation. Ways of partially purging the reaction mixture in order to remove the by-products formed on thermolysis are described in general form. No mention is made of any industrial use for these residues.

According to EP-A-0 061 013 (U.S. Pat. No. 4,388,246), the thermolysis of aliphatic, cycloaliphatic or aromatic polycarbamates is carried out at from 150° to 350° C. and at from 0.001 to 20 bar in the presence of inert solvents, in the presence or absence of catalysts and hydrogen chloride, organic acid chlorides, alkylating substances or organotin(IV) chlorides as aids. The by-products formed can be removed continuously from the reactor, for example with the reaction solution, and a corresponding amount of fresh or recovered solvent simultaneously metered in. Disadvantages in this process are, for example, that the use of refluxing solvent results in a reduction in the space-time yield of polyisocyanates and, in addition, a large amount of energy is necessary, including, for example, for recovery of the solvents. Furthermore, the aids employed, which are volatile under the reaction conditions, may result in contamination of the cleavage products. Also striking is the amount of residues, which is high relative to the polyisocyanate formed and, like the low operating pressure, casts doubt on the economic efficiency and reliability of the procedure in industry.

A process for the continuous thermolysis of carbamates, e.g. the cycloaliphatic diurethane 5-(ethoxycarbonylamino)-1-(ethoxycarbonylaminomethyl)-1,3,3-trimethylcyclohexane, which is fed along the inside of a tubular reactor in liquid form in the presence of a high-boiling solvent, is described in EP-B-92 738 (U.S. Pat. No. 4,692,550). This process has the disadvantages of low yields and low selectivity in the preparation of (cyclo)aliphatic diisocyanates. No results are given for a continuous procedure with recovery of the recombined or partially cleaved carbamate, and the work-up of the solvent containing the by-products and catalyst is not mentioned.

EP-A-0 355 443 relates to a circulation process for the preparation of (cyclo)aliphatic diisocyanates by conversion of the corresponding diamines into diurethanes and thermolysis of the latter. This process minimizes the reductions in yield by recycling the product from the urethane cleavage step after reaction with alcohol into the urethanization step. Non-recyclable by-products are removed by distillative separation of the urethanization product mixture, the worthless residue being produced as the bottom product and all relatively low-boiling components, including the diurethane, being removed at the top of the column.

This procedure, which involves high investment costs, also has the disadvantage of using large amounts of energy, since all the diurethane must be evaporated in the presence of catalysts, and, in addition, this must be done at a temperature level which is in the region of the urethane cleavage temperature. The isocyanate groups which form in the useful product react with the urethane groups of the residue to form relatively high-molecular-weight, yield-reducing by-products.

It is an object of the present invention to prepare distillable organic polyisocyanates, preferably aliphatic and cycloaliphatic diisocyanates, in high selectivity and in high space-time yields in an inexpensive and simple manner without using expensive and/or hazardous starting materials or aids.

We have found that, surprisingly, this object is achieved by partial purging of worthless by-products before the polyurethane cleavage.

The present invention accordingly provides a multistep process for the continuous preparation of organic polyisocyanates, preferably aliphatic or cycloaliphatic diisocyanates, by reacting the corresponding organic polyamines, preferably aliphatic or cycloaliphatic diamines, with carbonic acid derivatives and alcohols to give polyurethanes, preferably diurethanes, and thermolysis thereof, which comprises a) reacting organic polyamines, preferably aliphatic or cycloaliphatic diamines, with urea and alcohols in the absence or preferably in the presence of dialkyl carbonates, alkyl carbamates or mixtures of dialkyl carbonates and alkyl carbamates, and in the absence or preferably in the presence of catalysts to give polyurethanes, preferably diurethanes, and simultaneously removing the resultant ammonia, b) removing the alcohol, the dialkyl carbonates and/or alkyl carbamates from the resultant reaction mixture and preferably recycling them into reaction step a), c) dividing the polyurethane-containing reaction mixture, preferably the aliphatic or cycloaliphatic diurethane-containing reaction mixture, separating one part, by distillation, into a useful product, which contains the polyurethanes, preferably diurethanes, and the relatively low-boiling by-products and is then combined with the other part of the reaction mixture, and a worthless residue, which is removed from the preparation process, d) continuously pyrolyzing some of the combined, polyurethane-containing reaction mixture, preferably the aliphatic or cycloaliphatic diurethane-containing reaction mixture, in the liquid phase in the absence of solvents in the presence of catalysts at from 200° to 300° C. and at from 0.1 to 200 mbar, and removing the unthermolyzed component of the reaction mixture together with the resultant by-products and recycling these into reaction step a), e) separating the thermolysis products into a crude polyisocyanate, preferably a crude aliphatic or cycloaliphatic diisocyanate, and alcohol by rectification, and f) purifying the crude polyisocyanate, preferably the crude aliphatic or cycloaliphatic diisocyanate, by distillation.

In a preferred embodiment, the top fraction produced on distillative purification of the crude polyisocyanate (f) is recycled into reaction step (a), the side fraction, which essentially comprises pure polyisocyanate, is fed to a storage tank, and the bottom fraction is recycled into reaction step (a) or (d) or (a) and (d).

The process according to the invention allows distillable organic polyisocyanates, preferably aliphatic or cycloaliphatic diisocyanates, to be prepared easily in very good yields. The multistep process according to the invention has the advantages, in particular, of simple separation and removal or recycling of the dialkyl carbonates and/or alkyl carbamates formed as intermediates and of the alcohol and removal of the worthless, high-boiling by-products by partial purging of high-boiling components.

In purely formal terms, the process according to the invention can thus be balanced schematically by means of the following equation:

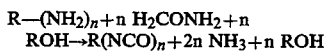

$$ROH \rightarrow R(NCO)_n + 2n\ NH_3 + n\ ROH$$

a) To prepare the monomeric polyurethanes, preferably (cyclo)aliphatic diurethanes, in reaction step (a), the polyamines, preferably diamines, are reacted with urea and an alcohol, expediently in an NH$_2$ group-:urea: alcohol ratio of from 1:0.9 to 1.3:1 to 5, preferably from 1:1.0 to 1.2:1.5 to 3, in the absence or preferably in the presence of dialkyl carbonates or preferably carbamates or mixtures of dialkyl carbonates and carbamates, and in the absence or preferably in the presence of catalysts at from 160° to 300° C., preferably at from 180° to 250° C., in particular at from 185° to 240° C., and at a pressure from 0.1 to 60 bar, preferably from 1 to 40 bar, depending on the alcohol used. These reaction conditions give reaction times of from 0.5 to 50 hours, preferably from 3 to 15 hours.

Amines which are suitable for the preparation of the monomeric polyurethanes which can be used according to the invention as intermediates are those of the formula R(NH$_2$)$_n$ where R is a polyvalent, preferably divalent, organic radical, e.g. a substituted or unsubstituted, for example alkyl-substituted, aromatic or preferably linear or branched aliphatic or substituted or unsubstituted cycloaliphatic radical. Specific examples of aromatic polyamines are 2,4- and 2,6-tolylenediamine, 4,4'- 2,4'- and 2,2'-diaminodiphenylmethanes and the corresponding isomer mixtures. Examples of suitable aliphatic or cycloaliphatic polyamines are: 1,4-butanediamine, 2-ethyl-1,4-butanediamine, 1,8-octanediamine, 1,10-decanediamine, 1,12-dodecanediamine, 1,4-cyclohexanediamine, 2-methyl- and 4-methyl-1,3-cyclohexanediamine, 1,3- and 1,4-diaminomethylcyclohexane- Preference is given to 2-methyl-1,5-pentanediamine, 2,2,4- and 2,4,4-trimethyl-1,6-hexanediamine and in particular 1,6-hexanediamine and 3-aminomethyl-3,5,5-trimethylcyclohexylamine.

Suitable alcohols are in principle all aliphatic alcohols, but preference is given to those whose boiling points are sufficiently far from the boiling point of the polyisocyanate, preferably diisocyanate, obtained by thermolysis, so that highly quantitative separation of the thermolysis products, polyisocyanate, preferably diisocyanate, and alcohol, is possible.

For these reasons, preference is therefore given to alcohols such as methanol, ethanol, n-propanol, n-butanol, isobutanol, n-pentanol, isopentanol, n-hexanol, isohexanols, cyclohexanol, 2-ethylhexanol, decanol or mixtures of said alcohols, but in particular n-butanol and/or isobutanol.

As stated above, the reaction in step (a) is preferably carried out in the presence of dialkyl carbonates, expediently in an amount of from 0.1 to 30 mol %, preferably from 1 to 10 mol %, or preferably alkyl carbamates, expediently in an amount of from 1 to 20 mol preferably from 5 to 15 mol %, based on the polyamine, preferably diamine. However, particular preference is given to mixtures of dialkyl carbonates and alkyl carbamates in said mixing ratios. Preferred dialkyl carbonates and/or carbamates are those whose alkyl radicals correspond to the alkyl radical of the alcohol used.

In order to increase the reaction rate, the monomeric polyurethanes, preferably diurethanes, can be prepared in the presence of catalysts. These are expediently used in amounts of from 0.01 to 20% by weight, preferably from 0.05 to 10% by weight, in particular from 0.1 to 5% by weight, based on the weight of the polyamine, preferably diamine. Suitable catalysts are inorganic or organic compounds which contain one or more cations, preferably one cation of metals from groups IA, IB, IIA, IIB, IIIA, IIIb, IVA, IVB, VA, VB, VIB, VIIB and VIIIB of the Periodic Table, as defined in Handbook of Chemistry and Physics, 14th Edition, published by Chemical Rubber Publishing Co., 23 Superior Ave. N.E., Cleveland, Ohio, for example halides, such as chlorides and bromides, sulfates, phosphates, nitrates, borates, alkoxides, phenoxides, sulfonates, oxides, oxide hydrates, hydroxides, carboxylates, chelates, carbonates, thiocarbamates and dithiocarbamates. Specific examples which may be mentioned are the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron and cobalt. The catalysts can also be used, without detectable disadvantages, in the form of their hydrates or ammoniates.

Specific examples of typical catalysts are: lithium methoxide, lithium ethoxide, lithium propoxide, lithium butoxide, sodium methoxide, potassium tertbutoxide, magnesium methoxide, calcium methoxide, tin(II) chloride, tin(IV) chloride, lead acetate, lead phosphate, antimony(III) chloride, antimony(V) chloride, aluminum acetylacetonate, aluminum isobutylate, aluminum trichloride, bismuth(III) chloride, copper(II) acetate, copper(II) sulfate, copper(II) nitrate, bis(triphenylphosphinoxido)copper(II) chloride, copper molybdate, silver acetate, gold acetate, zinc oxide, zinc chloride, zinc acetate, zinc acetylacetonate, zinc octanoate, zinc oxalate, zinc hexylate, zinc benzoate, zinc undecylenate, cerium(IV) oxide, uranyl acetate, titanium tetrabutoxide, titanium tetrachloride, titanium tetraphenoxide, titanium naphthenate, vanadium(III) chloride, vanadium acetylacetonate, chromium(III) chloride, molybdenum(VI) oxide, molybdenum acetylacetonate, tungsten(VI) oxide, manganese(II) chloride, manganese(II) acetate, manganese(III) acetate, iron(II) acetate, iron(III) acetate, iron phosphate, iron oxalate, iron(III) chloride, iron(III) bromide, cobalt acetate, cobalt chloride, cobalt sulfate, cobalt naphthenate, nickel chloride, nickel acetate and nickel naphthenate, and mixtures thereof.

It has proven advantageous for the resultant ammonia to be removed immediately from the reaction mixture, for example by distillation. The apparatus used for this purpose, for example a distillation column, is operated at from 60° to 150° C., preferably at from 65° to 120° C., so that a coating of ammonium carbamate, which is formed in small amounts from ammonia and carbon dioxide due to decomposition of urea, can be avoided.

b) The alcohol, the dialkyl carbonates, if formed or present in the reaction mixture, or alkyl carbamates, or mixtures of at least two of these components, are removed from the reaction mixture (a) obtained by, advantageously, continuous reaction, and preferably recycled into reaction step (a). In order to remove the components, the reaction mixture is advantageously decompressed from the pressure level of step (a) to a pressure in the range from 1 to 500 mbar, preferably from 10 to 100 mbar. This gives gaseous vapors which contain most of the alcohol and from 0 to 30% by weight, preferably from 1 to 10% by weight, of dialkyl carbonate and/or from 1 to 50% by weight, preferably from 1 to 20% by weight, of alkyl carbamate, and a liquid product which essentially comprises the monomeric polyurethane, preferably diurethane, and possibly contains oligourea-polyurethanes and high-boiling oligomers.

The vapors obtained are separated in subsequent, expediently distillative, purification steps, preferably by rectification, and the useful products (alcohol and alkyl carbamate) isolated in this operation are preferably recycled, individually or as a mixture, into reaction step (a) for formation of the monomeric polyurethanes.

c) The liquid reaction mixture (c) containing the monomeric polyurethanes, preferably diurethanes, and possibly oligourea-polyurethanes and high-boiling oligomers which is obtained in reaction step (b) after removal of the vapors is divided into two sub-streams in a weight ratio of from 5 to 50:95 to 50 parts by weight, preferably from 10 to 30:90 to 70 parts by weight. One of the two portions of equal size or preferably the smaller portion is separated by distillation in a conventional distillation unit, preferably a thin-film evaporator, at from 170° to 240° C., preferably at from 180° to 230° C., and at from 0.01 to 5 mbar, preferably from 0.1 to 2 mbar, into a useful product containing the polyurethanes, preferably diurethanes, and the relatively low-boiling by-products, and undistillable by-products, which are removed from the preparation process and usually discarded as worthless residue. The useful product is combined with the other portion, of equal size or preferably larger, and the combined reaction mixture containing polyurethanes, preferably diurethanes, is fed to thermolysis.

This measure in step (c) limits the proportion of undistillable by-products in the reaction mixture, which form in the successive sub-reactions and would constantly accumulate in the reaction cycle due to recycling of useful starting materials, to a content of from 3 to 30% by weight, preferably from 5 to 20% by weight, and thus ensures that the reaction proceeds in high selectivity and without interruptions.

d) The reaction mixture containing polyurethanes, preferably diurethanes, obtained in reaction step (c) is partially continuously thermolyzed in a suitable apparatus in the absence of solvent in a liquid phase in the presence of catalysts at from 200° to 300° C., preferably from 220° to 280° C., and under a reduced pressure of from 0.1 to 200 mbar, preferably from 5 to 80 mbar. The conversion of polyurethane to polyisocyanate, preferably of diurethane to diisocyanate, in the thermolysis apparatus can be selected substantially freely depending on the polyurethane used and is expediently in the range from 10 to 95% by weight, preferably from 40 to 85% by weight, of the polyurethane feed. The unthermolyzed component of the reaction mixture, which contains unreacted polyurethanes, oligourea-polyurethanes, high-boiling oligomers and other reusable and worthless by-products, is separated off, purged continuously from the thermolysis apparatus and recycled directly or, if desired, after reaction with alcohol, into reaction step (a).

Examples of catalysts used for the chemical cleavage of the polyurethanes are the above-mentioned inorganic and organic compounds which catalyze the formation of urethanes.

Compounds which have proven particularly successful and are therefore preferred are dibutyltin dilaurate, iron (III) acetylacetonate, cobalt (II) acetylacetonate, zinc acetylacetonate and tin(II) dioctanoate.

Examples of suitable thermolysis apparatuses are cylindrical reactors, e.g. tubular furnaces or preferably evaporators, for example thin-film or bulk evaporators, e.g. Robert evaporators, Herbert evaporators, caddle-type evaporators and preferably heated cartridge evaporators.

e) The products formed on thermolysis, which are composed principally of alcohol, polyisocyanate, preferably diisocyanate, and partially cleaved polyurethanes, are then separated into alcohol and a crude polyisocyanate mixture having a polyisocyanate content of from 85 to 99% by weight, preferably from 95 to 99% by weight, advantageously with the aid of one or more distillation columns, preferably by rectification, at from 100° to 220° C., preferably from 120° to 170° C., and at from 1 to 200 mbar, preferably at from 5 to 50 mbar. The relatively high-boiling by-products obtained on distillative separation and in particular the uncleaved and partially cleaved polyurethanes are preferably recycled into the thermolysis apparatus.

f) The crude polyisocyanate mixture preferably obtained by rectification is purified by distillation at from 100° to 180° C. and at from 1 to 50 mbar, the individual fractions being recycled or isolated as pure product. In the case of purification distillation, which is preferred, the top fraction, which preferably comprises polyisocyanate, in particular diisocyanate, is, as stated above, recycled into reaction step (a), the polyurethane formation, if appropriate after reaction of the free isocyanate groups with alcohol, the side fraction, which comprises pure polyisocyanate, in particular diisocyanate, preferably in a purity of at least 98% by weight, in particular greater than 99% by weight, is taken off and stored, and the bottom fraction, in which the essential components are the partially cleaved polyurethanes and polyisocyanates, is preferably recycled into the thermolysis apparatus. In other variants, however, the bottom fraction can be recycled into the distillation column (e) for removal of crude polyisocyanate and alcohol or into reaction step (a), the polyurethane formation. It is also possible to divide the bottom fraction into 2 or 3 product streams, which are preferably recycled into the polyurethane formation (a) and the thermolysis apparatus (d) and, if desired, into the distillation column (e).

The multistep process according to the invention for the continuous preparation of organic polyisocyanates with recycling and purging of by-products allows distillable polyisocyanates, preferably diisocyanate, to be prepared in high selectivity and very good yield. The process according to the invention is particularly suitable for the preparation of aliphatic diisocyanates, such as 2-methylpentane 1,5-diisocyanate, isomeric aliphatic diisocyanates having 6 carbon atoms in the alkylene radical, and mixtures thereof, and preferably hexamethylene 1,6-diisocyanate, and cycloaliphatic diisocyanates, in particular 3-isocyanatomethyl-3,5,5-trimethylcyclohexyl isocyanate, by an economical method.

The polyisocyanates prepared are eminently suitable for the preparation of plastics containing urethane, isocyanurate, amide and/or urea groups by the polyisocyanate polyaddition process. They are furthermore used for the preparation of polyisocyanate mixtures which have been modified by means of urethane, biuret and/or isocyanurate groups. Such polyisocyanate mixtures of aliphatic or cycloaliphatic diisocyanates are used in particular for the production of light-stable polyurethane paints and coatings.

EXAMPLE 1

0.879 kg of urea, 0.805 kg of hexamethylene-1,6-diamine and 0.089 kg of n-butanol, as well as 3.333 kg of a product mixture containing cleavage butanol, part of the reaction mixture from the cleavage of urethane, containing the resultant by-products, which principally comprised relatively high-molecular-weight compounds containing isocyanurate, allophanate, urea and polyurethane groups, and the top fraction from the purification distillation of hexamethylene diisocyanate, were added per hour at 220°–230° C. and 12 bar into the first reactor of a three-stage stirred reactor cascade fitted with heated columns and head condensers and a pressure-retention means, containing a mixture of hexamethylene-1,6-dibutylurethane and n-butanol in addition to hexamethylene-oligourea-polybutylurethanes, dibutyl carbonate and butyl carbamate. The resultant ammonia escaping from the refluxing reaction mixture was removed via the columns and freed virtually quantitatively from butanol in the downstream condensers by fractional condensation.

The product from the 3rd reactor in the cascade was continuously decompressed in a tank operated at 50 mbar. The gaseous vapors passed directly into a rectification column, likewise operated at 50 mbar, from which about 2.8 kg/h of n-butanol were obtained at the top, 0.06 kg/h of a dibutyl carbonate-rich azeotrope were obtained at the side and 0.234 kg/h of butyl carbamate were obtained in the stripping section. The n-butanol and the butyl carbamate were recycled into the reactor cascade.

The liquid product from the decompression tank was divided in the approximate weight ratio 3:1, and the smaller part was fed to a thin-film evaporator, which was operated at 220° C. and 1 mbar, giving 0.071 kg/h of undistillable residue at the bottom (purging of high-boiling components). The hexamethylene-1,6-dibutylurethane which condensed at the top was combined with the majority of the liquid product from the decompression tank, the dibutyltin dilaurate catalyst unavoidably removed with the residue was replaced, and the product was fed in the melt-liquid state via a metering device to a steam-heated evaporator reactor with a reaction capacity of 2.5 l for homogeneously catalyzed thermolysis. The thermolysis at a conversion of about 55% with respect to the 3.81 kg/h of hexamethylene-1,6-dibutylurethane employed was carried out at 30 mbar with vigorous boiling of the reaction mixture. The gaseous vapors were passed, for separation, into a rectification column, from the top of which 1.1 kg/h of liquid cleavage butanol were removed. Approximately 95% by weight crude diisocyanate was obtained at the side. Uncleaved diurethane and 6-isocyanatohexylbutylurethane were recycled into the evaporator reactor.

The crude hexamethylene 1,6-diisocyanate obtained in this way was subjected to purification distillation, 1.115 kg/h of hexamethylene 1,6-diisocyanate having a purity of >99% being obtained at the side of a column operated at 30 mbar. The bottom product from the purification distillation, which was predominantly composed of 6-isocyanatohexylbutylurethane and its relatively high-molecular-weight oligomers, was recycled directly into the evaporator reactor or into the subsequent rectification column.

The top product from the purification distillation, combined with the cleavage butanol and the product from the urethane Cleavage evaporator reactor, which contained the high-boiling by-products, was passed directly back into reaction step a), the three-stage stirred reactor cascade. The overall selectivity for the conversion of hexamethylene-1,6-diamine feed into hexamethylene 1,6-diisocyanate was 97%.

EXAMPLE 2

The procedure was similar to that of Example 1, but the hexamethylenediamine derivatives in the stirred reactor cascade were replaced by corresponding 2-methylpentamethylene-1,5-diamine derivatives, dibutyl carbonate and butyl carbamate. 0.886 kg of urea, 0.810 kg of 2-methylpentamethylene-1,5-diamine and 0.097 kg of n-butanol, as well as 3.543 kg of a product mixture of cleavage butanol, part of the reaction mixture from the cleavage of urethane and the top fraction from the purification distillation of diisocyanate were added per hour to this mixture at from 220° to 230° C. and at 12 bar.

The product from the 3rd reactor in the cascade was decompressed at 50 mbar, and the vapors were fed in gas form into a rectification column; about 2.8 kg/h of n-butanol were obtained at the top, 0.06 kg/h of a dibutyl carbonate-rich azeotrope were obtained at the side and 0.245 kg of butyl carbamate were obtained in the stripping section. The n-butanol and the butyl carbamate were recycled into the reactor cascade.

0.087 kg/h of undistillable residue were obtained in the bottom of the thin-film evaporator for partial removal of high-boiling components.

The cleavage of urethane at a conversion of about 55% with respect to the 3.80 kg/h of 2-methylpentamethylene-1,5-diurethane employed was carried out at 30 mbar. 1.1 kg/h of liquid cleavage butanol were obtained at the top of the downstream rectification column and about 95% by weight crude diisocyanate was obtained at the side. Purification distillation gave 1.110 kg/h of 2-methylpentamethylene 1,5-diisocyanate. This gave an overall selectivity for the conversion of 2-methylpentamethylene-1,5-diamine feed into 2-methylpentamethylene 1,5-diisocyanate of 96%.

EXAMPLE 3

The procedure was similar to that of Example 1, but the hexamethylenediamine derivatives in the stirred reactor cascade were replaced by corresponding 3-aminomethyl-3,5,5-trimethylcyclohexylamine derivatives, dibutyl carbonate and butyl carbamate. 0.625 kg of urea, 0.839 kg of 3-aminomethyl-3,5,5-trimethylcyclohexylamine and 0.061 kg of n-butanol, as well as 2.297 kg of a product mixture of cleavage butanol, part of the reaction mixture from the cleavage of urethane and the top fraction from the purification distillation of diisocyanate were added per hour to this mixture at from 220° to 230° C. and at 12 bar.

The product from the 3rd reactor in the cascade was decompressed at 50 mbar, and the vapors were fed in gas form into a rectification column; about 2.1 kg/h of n-butanol were obtained at the top, 0.05 kg/h of a dibutyl carbonate-rich azeotrope were obtained at the side and 0.175 kg of butyl carbamate were obtained in the stripping section. The n-butanol and the butyl carbamate were recycled into the reactor cascade.

0.044 kg/h of undistillable residue were obtained in the bottom of the thin-film evaporator for partial removal of high-boiling components.

The cleavage of urethane at a conversion of about 60% with respect to the 2.94 kg/h of 3-urethanomethyl-3,5,5-trimethylcyclohexylurethane employed was carried out at 20 mbar. 0.81 kg/h of liquid cleavage butanol were obtained at the top of the downstream rectification column and about 95% by weight crude diisocyanate was obtained at the side. Purification distillation gave 1.060 kg/h of 3-isocyanatomethyl-3,5,5-trimethylcyclohexyl isocyanate. This gave an overall selectivity for the conversion of 3-aminomethyl-3,5,5-trimethylcyclohexylamine feed into 3-isocyanatomethyl-3,5,5-trimethylcyclohexyl isocyanate of 98%.

EXAMPLE 4

The procedure was similar to that of Example 1, but the hexamethylenediamine derivatives in the stirred reactor cascade were replaced by corresponding 2,2,4(2,4,4)-trimethylhexamethylene-1,6-diamine derivatives, dibutyl carbonate and butyl carbamate. 0.746 kg of urea, 0.923 kg of 2,2,4(2,4,4)-trimethylhexamethylene-1,6-diamine and 0.088 kg of n-butanol, as well as 3.379 kg of a product mixture of cleavage butanol, part of the reaction mixture from the cleavage of urethane and the top fraction from the purification distillation of diisocyanate were added per hour to this mixture at from 220° to 230° C. and at 12 bar.

The product from the 3rd reactor in the cascade was decompressed at 50 mbar, and the vapors were fed in gas form into a rectification column; about 2.9 kg/h of n-butanol were obtained at the top, 0.06 kg/h of a dibutyl carbonate-rich azeotrope were obtained at the side and 0.239 kg of butyl carbamate were obtained in the stripping section. The n-butanol and the butyl carbamate were recycled into the reactor cascade.

0.074 kg/h of undistillable residue were obtained in the bottom of the thin-film evaporator for partial removal of high-boiling components.

The cleavage of urethane at a conversion of about 50% with respect to the 3.99 kg/h of 2,2,4(2,4,4)-trimethylhexamethylene-1,6-diamine employed was carried out at 30 mbar. 0.95 kg/h of liquid cleavage butanol were obtained at the top of the downstream rectification column and about 95% by weight crude diisocyanate was obtained at the side. Purification distillation gave 1.170 kg/h of 2,2,4(2,4,4)-trimethylhexamethylene 1,6-diisocyanate. This gave an overall selectivity for the conversion of 2,2,4(2,4,4)-trimethylhexamethylene-1,6-diamine feed into 2,2,4(2,4,4)-trimethylhexamethylene 1,6-diisocyanate of 97%.

EXAMPLE 5

The procedure was similar to that of Example 1, but the urethanization reaction was carried out using a reaction system comprising a reactor fitted with heated column and head condenser and a downstream reaction column containing 10 trays. About 2.8 kg/h of n-butanol vapor were fed into the bottom of the reaction column and passed in gas form in countercurrent to the liquid product stream. n-Butanol vapors from the top of the reaction column passed directly into the vapor space of the reactor.

The starting materials and the recycling streams from the other reaction steps were fed into the reactor.

The liquid reaction product from the reaction column was decompressed continuously in a tank operated at 50 mbar.

EXAMPLE 6

The procedure was similar to that of Example 1, but the reaction mixture obtained from the urethane synthesis was fed into a column operated at 500 mbar. About 1.7 kg/h of n-butanol were removed from the top of this n-butanol column. The n-butanol was not condensed, but fed, after superheating, into the bottom of a downstream stripping column operated at 100 mbar. The bottom product from the n-butanol column was fed to the top of the stripping column and freed from residual n-butanol, but in particular from dibutyl carbonate and butyl carbamate, by the n-butanol vapor rising in countercurrent.

The liquid product from the stripping column was divided approximately in the weight ratio 3:1 and fed both to the thin-film evaporator for partial removal of high-boiling components and to the cleavage of urethane.

The gaseous vapors from the stripping column passed into a rectification column operated at 50 mbar for separation into the discharge streams n-butanol, dibutyl carbonate and butyl carbamate mentioned in Example 1.

EXAMPLE 7

The procedure was similar to that of Example 1, but the gaseous vapors from the cleavage of urethane were passed into a first rectification column at the top of which gaseous n-butanol and diisocyanate were obtained. This gaseous stream passed into the purification distillation column comprising a main column, at the top of which 1.1 kg/h of liquid cleavage butanol were obtained, and an ancillary column, which gave 1.115 kg/h of hexamethylene 1,6-diisocyanate at the side.

The n-butanol top product from the main column and the top product from the ancillary column, combined with the product from the urethane cleavage evaporator reactor, which contained the high-boiling by-products, passed directly back into reaction step a), the three-stage reactor cascade.

The bottom product from the purification distillation column served as reflux for the rectification column downstream of the urethane cleavage.

We claim:

1. A multistep process for the continuous preparation of organic polyisocyanates by reacting the corresponding organic polyamines with carbonic acid derivatives and alcohols to give polyurethanes, and thermolysis thereof, which comprises
    a) reacting organic polyamines with urea and alcohols in the presence or absence of dialkyl carbonates and/or alkyl carbamates and in the presence or absence of catalysts to give polyurethanes, and simultaneously removing the resultant ammonia,
    b) removing the alcohol, the dialkyl carbonates and/or alkyl carbamates from the resultant reaction mixture,
    c) dividing the polyurethane-containing reaction mixture into a first part and a second part, separating the first part of said reaction mixture by distillation into: (i) a mixture of the polyurethanes and the relatively low-boiling by-products and (ii) a residue, which is removed from the preparation process, and combining the mixture (i) with the second part of the polyurethane-containing reaction mixture, d) continuously pyrolizing some of the combined, polyurethane-containing reaction mixture in the liquid phase in the absence of solvents in the presence of catalysts at a temperature of from 200° to 300° C. and at a pressure of from 0.1 to 200 mbar, and removing the unthermolyzed component of the reaction mixture together with the resultant by-products and recycling these into reaction step a), e) separating the thermolysis products into a crude polyisocyanate mixture and alcohol by rectification, and f) purifying the crude polyisocyanate by distillation.

2. A multistep process as claimed in claim 1, wherein the crude polyisocyanate (f) is purified by distillation, where
the top fraction is recycled into reaction step (a),
the side fraction comprises essentially pure polyisocyanate, and
the bottom fraction is recycled into reaction step (a) or (d) or (a) and (d).

3. A multistep process for the continuous preparation of aliphatic or cycloaliphatic by reacting the corresponding diamines with carbonic acid derivatives and alcohols to give diurethanes, and thermolysis thereof, which comprises
   a) reacting aliphatic or cycloaliphatic diamines with urea and alcohols in the presence or absence of dialkyl carbonates and/or alkyl carbamates and in the presence or absence of catalysts to give polyurethanes, and simultaneously removing the resultant ammonia,
   b) removing the alcohol, the dialkyl carbonates and/or alkyl carbamates from the resultant reaction mixture,
   c) dividing the diurethane-containing reaction mixture into a first part and a second part, separating the first part of said reaction mixture by distillation into: (i) a mixture of the diurethanes and the relatively low-boiling by-products and (ii) a residue, which is removed from the preparation process, and combining the mixture (i) with the second part of the diurethane-containing reaction mixture,
   d) continuously pyrolizing some of the combined, diurethane-containing reaction mixture in the liquid phase in the absence of solvents in the presence of catalysts at from a temperature of 200° to 300° C. and at a pressure of from 0.1 to 200 mbar, and removing the unthermolyzed component of the reaction mixture together with the resultant by-products and recycling these into reaction step a),
   e) separating the thermolysis products into a crude diisocyanate mixture and alcohol by rectification, and
   f) purifying the crude diisocyanate by distillation.

4. A multistep process as claimed in claim 3, wherein the crude diisocyanate (e) is purified by distillation, where
the top fraction is recycled into reaction step (a),
the side fraction comprises essentially pure diisocyanate, and
the bottom fraction is recycled into reaction step (a) or (d) or (a) and (d).

5. A multistep process as claimed in claim 3, wherein the diurethane-containing reaction mixture (c) is divided in a weight ratio of from 5 to 50:95 to 50, and the first-mentioned, relatively small part of the reaction mixture is separated by distillation.

6. A multistep process as claimed in claim 3, wherein the resultant reaction mixture (b) is decompressed from between 1 and 40 bar to between 1 and 500 mbar in order to remove the alcohol, the dialkyl carbonates and/or alkyl carbamates.

7. A multistep process as claimed in claim 3, wherein the aliphatic diamines used are hexamethylene-1,6-diamine and/or isomeric aliphatic diamines having 6 carbon atoms in the alkylene radical.

8. A multistep process as claimed in claim 3, wherein the cycloaliphatic diamines used are 3-aminomethyl-3,5,5-trimethylcyclohexylamine.

9. A multistep process as claimed in claim 1 wherein the alcohol, dialkyl carbonates, and/or alkyl carbamates removed from the reaction mixture of step b) are recycled to reaction step a).

10. A multistep process as claimed in claim 1 wherein the alcohol, dialkyl carbonates, and/or alkyl carbamates removed from the reaction mixture of step b) are recycled to reaction step a).

* * * * *